US012521262B2

(12) United States Patent
Murphy

(10) Patent No.: US 12,521,262 B2
(45) Date of Patent: Jan. 13, 2026

(54) STENT DELIVERY SYSTEM AND HANDLING DEVICE FOR A STENT DELIVERY SYSTEM

(71) Applicant: B. Braun Melsungen AG, Melsungen (DE)

(72) Inventor: Bryan Murphy, Wicklow (IE)

(73) Assignee: B. Braun Melsungen AG, Melsungen (DE)

( * ) Notice: Subject to any disclaimer, the term of this patent is extended or adjusted under 35 U.S.C. 154(b) by 684 days.

(21) Appl. No.: 17/913,985

(22) PCT Filed: Mar. 5, 2021

(86) PCT No.: PCT/EP2021/055634
§ 371 (c)(1),
(2) Date: Sep. 23, 2022

(87) PCT Pub. No.: WO2021/190901
PCT Pub. Date: Sep. 30, 2021

(65) Prior Publication Data

US 2023/0346579 A1 Nov. 2, 2023

(30) Foreign Application Priority Data

Mar. 26, 2020 (EP) ..................................... 20165757

(51) Int. Cl.
*A61F 2/95* (2013.01)
*A61F 2/82* (2013.01)
(Continued)

(52) U.S. Cl.
CPC .......... *A61F 2/9517* (2020.05); *A61F 2/9522* (2020.05); *A61F 2/966* (2013.01); *A61M 25/0147* (2013.01); *A61F 2002/826* (2013.01)

(58) Field of Classification Search
CPC ...... A61F 2/9517; A61F 2/9522; A61F 2/966; A61F 2002/826; A61F 2/95; A61M 25/0147
See application file for complete search history.

(56) References Cited

U.S. PATENT DOCUMENTS

2010/0036472 A1 2/2010 Papp
2015/0057739 A1* 2/2015 Costello ................ A61F 2/9517 623/1.11
(Continued)

FOREIGN PATENT DOCUMENTS

WO 2019053508 A1 3/2019

OTHER PUBLICATIONS

Office Action received in European Application No. 21 708 698.2-1113 dated Nov. 24, 2022, 6 pages.
(Continued)

*Primary Examiner* — Jerrah Edwards
*Assistant Examiner* — Jose H. Trevino, III
(74) *Attorney, Agent, or Firm* — Christopher A Rothe; CM Law

(57) ABSTRACT

A stent delivery system includes a handling device having a housing, a thumbwheel rotatably mounted in the housing, and a winding spool rotatable with the thumbwheel. A catheter arrangement has an inner shaft with an end fixed on the housing, an outer sheath disposed coaxially to the inner shaft, and a stent received radially between the inner shaft and outer sheath. A flexible pull member engages a proximal end of the outer sheath and is held on the winding spool to be windable. For release of the stent, the outer sheath is displaceable relative to the inner shaft by winding the flexible pull member on the winding spool. The winding spool has different winding diameters on which the flexible pull member engages and is windable in different displace-
(Continued)

ment positions of the outer sheath. Different transmission ratios result between rotation of the thumbwheel and movement of the outer sheath.

7 Claims, 6 Drawing Sheets

(51) Int. Cl.
*A61F 2/966* (2013.01)
*A61M 25/01* (2006.01)

(56) References Cited

U.S. PATENT DOCUMENTS

| | | | |
|---|---|---|---|
| 2015/0094794 | A1 | 4/2015 | Cummins et al. |
| 2015/0250631 | A1 | 9/2015 | Cummins |

OTHER PUBLICATIONS

Search Report received in International Application No. PCT/EP2021/055634 dated Jun. 1, 2021, with translation, 5 pages.

* cited by examiner

STENT DELIVERY SYSTEM AND HANDLING DEVICE FOR A STENT DELIVERY SYSTEM

CROSS-REFERENCE TO RELATED APPLICATIONS

This application is the United States national stage entry of International Application No. PCT/EP2021/055634, filed Mar. 5, 2021, and claims priority to European Application No. 20165757.4, filed Mar. 26, 2020. The contents of International Application No. PCT/EP2021/055634 and European Application No. 20165757.4 are incorporated by reference herein in their entireties.

FIELD

The invention relates to a stent delivery system and to a handling device for a stent delivery system.

BACKGROUND

It is well known to employ intravascular endoprostheses delivered percutaneously for the treatment of diseases of various body vessels. Such intravascular endoprostheses are commonly referred to as "stents". A stent is a generally longitudinal tubular device of biocompatible material having holes or slots that define a flexible framework that allows radial expansion of the stent, by a balloon catheter or the like, or alternatively by self-expansion due to shape memory characteristics of the material within the body vessel. The flexible framework is configured to allow the stent to be compressed into a smaller outer diameter so that it can be mounted inside a stent delivery system.

The stent delivery system is used to convey the stent to a desired location within the body vessel, and then to release the stent in position. Upon release the stent may self-expand into a larger outer diameter.

WO 2019/053508 A1 discloses a stent delivery system having a handling device and a catheter arrangement. The catheter arrangement comprises an inner shaft, an outer sheath disposed coaxially to the inner shaft, and a stent which is received radially between the inner shaft and the outer sheath. The inner shaft of the catheter arrangement has a proximal end that is fixed to a housing of the handling device. The stent delivery system further comprises a flexible pull member which, with one end, engages on a proximal end of the outer sheath and, with the other end, is held on a winding spool of the handling device. The winding spool is operatively connected to a thumbwheel that is rotatably mounted inside the housing of the handling device. For release of the stent, the thumbwheel is rotated manually, whereby the winding spool is rotated. The flexible pull member engaging on the winding spool is thereby wound onto the winding spool and, as a result, the outer sheath is displaced relative to the inner shaft in the proximal direction. Due to this proximal retraction of the outer sheath, the stent is released and, thus, can expand within the blood vessel.

SUMMARY

It is the object of the present invention to provide a stent delivery system that allows a simplified handling during the release of the stent. It is further the object of the present invention to provide a handling device for such a stent delivery system, the handling device allowing a simplified handling during the release of the stent.

According to a first aspect, a stent delivery system is provided comprising: a handling device having a housing, a thumbwheel mounted in the housing to be rotatable, and a winding spool rotating together with the thumbwheel; a catheter arrangement having an inner shaft, with a proximal end of the shaft fixed on the housing, an outer sheath disposed coaxially to the inner shaft, and having at least a first stent which is received radially between the inner shaft and the outer sheath; a flexible pull member which, with one end, engages on a proximal end of the outer sheath and, with the other end, is held on the winding spool to be windable; wherein, for release of at least the first stent, the outer sheath is displaceable relative to the inner shaft in the proximal direction by means of winding the flexible pull member on the winding spool; wherein the winding spool has different winding diameters on which the flexible pull member engages and is windable in different displacement positions of the outer sheath, whereby different transmission ratios result between the rotation movement of the thumbwheel and the proximal displacing movement of the outer sheath. Owing to the solution according to the invention, in the different displacement positions of the outer sheath, different transmission ratios are achieved between the rotation movement of the thumbwheel and the proximal displacing movement of the outer sheath resulting therefrom. Depending on the transmission ratio, the outer sheath is displaced either in comparatively rough or fine, rapid or slow, respectively, manner in the proximal direction following the rotation movement of the thumbwheel. In other words, depending on the displacement position of the outer sheath, a relatively rough or fine controlling of the displacement move is achieved by means of the thumbwheel. Hereby, simplified handling during release of at least the first stent can be achieved.

In one embodiment, the different winding diameters of the winding spool are matched to different geometric properties of the catheter arrangement. The different geometric properties of the catheter arrangement may in particular be axial distance dimensions between different components and/or sections of the catheter arrangement. As an alternative or in addition, the different geometric properties may be axial length dimensions of different components and/or sections of the catheter arrangement.

In one embodiment, the different geometric properties are a first axial distance between a distal end of the inner shaft and the first stent, a first length of the first stent, a second axial distance between the first stent and a second stent, and/or a second length of the second stent. For example, a first winding diameter of the winding spool can be matched to the first axial distance between the distal end of the inner shaft and the first stent, and a second winding diameter of the winding spool can be matched to the first length of the first stent. Upon release of the first stent, the outer sheath is initially displaced along the first axial distance and subsequently along the first length relative to the inner shaft in the proximal direction. Due to the corresponding adaptation of the winding diameters, the proximal displacement for bridging the first axial distance can be made comparatively more rapid than during bridging of the first length, or vice versa. Moreover, a second stent can be received radially between the inner shaft and the outer sheath, and spaced proximally from the first stent. As an alternative or in addition, the different winding diameters of the winding spool can be matched to the second axial distance and/or the second length of the second stent. Preferably, the different winding diameters of the winding spool are matched to the above mentioned geometric properties of the catheter arrangement such that for proximal retracting of the outer sheath along the first axial distance, the first length, the second axial distance and/or the second length are in each case exactly one revolution of the thumbwheel is required. Preferably, the first axial distance is greater than the first length and/or the second axial distance and/or the second length. In this case, the first winding diameter is configured larger than the second winding diameter such that an equal amount of rotation of the thumbwheel is required to bridge the different axial distances and/or different lengths of the catheter arrangement. Preferably, this amount of rotation is exactly 360 degrees, i.e. one revolution. In other words, in this case one and the same amount of thumb wheel rotation is required in each case to bridge the first axial distance, the first length, the second axial distance and/or the second length.

In one embodiment, the different winding diameters are formed on different axial sections of the winding spool. The different axial sections are adjacent to each other in the axial direction of the winding spool. For example, a first axial section can have and/or produce a first winding diameter, and a second axial section can have and/or produce a second winding diameter. By means of actuating the thumbwheel, the flexible pull member is initially wound on the first winding diameter and, subsequently, wound on the second winding diameter, or vice versa. A transition between the different winding diameters can be continuous or stepped in the radial direction.

In one embodiment, the winding spool has at least a first winding diameter which the flexible pull member engages during a displacement move of the outer sheath between a first displacement position and a second displacement position, and a second winding diameter on which the flexible pull member engages during a displacement move of the outer sheath between the second displacement position and a third displacement position. For release of at least the first stent, the outer sheath is moved relative to the inner shaft in the proximal direction starting from the first displacement position to the second displacement position and, subsequently, further to the third displacement position. In that context, the flexible pull member initially cooperates with the first winding diameter of the winding spool. That is, during a displacement move starting from the first displacement position to the second displacement position, the flexible pull member is wound on the first winding diameter. As a result, a first transmission ratio between the rotation movement of the thumbwheel or the winding spool rotating together with the thumbwheel, respectively, and the displacing movement of the outer sheath is obtained. Upon a further proximal displacement starting from the second displacement position to the third displacement position, the flexible pull member cooperates with the second winding diameter and is wound thereon. As a result, a corresponding second transmission ratio is obtained. Due to these different transmission ratios, the outer sheath is displaced—during a constant rotational movement of the thumbwheel and, thus, also the winding spool—comparatively more rapidly between the first displacement position and the second displacement position than between the second displacement position and the third displacement position, or vice versa. Preferably, a first axial distance between the first and the second position and a second axial distance between the second and third position are matched to the first winding diameter and the second winding diameter such that the same amount of thumb wheel rotation, preferably exactly one revolution, is required to retract the outer sheath along the first and the second axial distance.

In one embodiment, the winding spool has a helical circumferential groove, with the groove bottom thereof providing the first winding diameter. During winding on the first winding diameter the flexible pull member is guided within the helical circumferential groove. Preferably, the helical circumferential groove extends over 360° along the circumference of the winding spool. In this embodiment of the invention, the first winding diameter is preferably larger than the second winding diameter. The helical circumferential groove is preferably disposed on a first axial section of the winding spool. Preferably, the helical circumferential groove is configured such that exactly one revolution of the thumbwheel is required to initially retract the outer sheath—starting from a delivery condition of the stent delivery system and/or the catheter arrangement—to the distal end of the first stent.

In one embodiment, the winding spool has a cylindrical section, with the outer diameter thereof providing the second winding diameter. The cylindrical section preferably has a circular cylindrical design. In this embodiment of the invention, the second winding diameter is preferably smaller than the first winding diameter. The cylindrical section is preferably disposed on a second axial section of the winding spool. Preferably, the cylindrical section is configured such that exactly one revolution of the thumbwheel is required to further retract the outer sheath—starting from the distal end of the first stent—to release the first stent and, in case further stents are provided, each further stent.

According to a second aspect, a handling device for a stent delivery system is provided, the handling device having a housing, a thumbwheel mounted in the housing to be rotatable, and a winding spool rotating together with the thumbwheel, wherein the winding spool has different winding diameters. In order to avoid repetitions, referral and explicit reference is made to the description of the stent delivery system according to the first aspect and its embodiments. The explanations given there apply correspondingly to the handling device according to the second aspect.

BRIEF DESCRIPTION OF THE DRAWINGS

In the following, an embodiment of the invention will be described in detail with reference to the drawings. Throughout the drawings, the same elements will be denoted by the same reference numerals.

DETAILED DESCRIPTION

Figure 1:
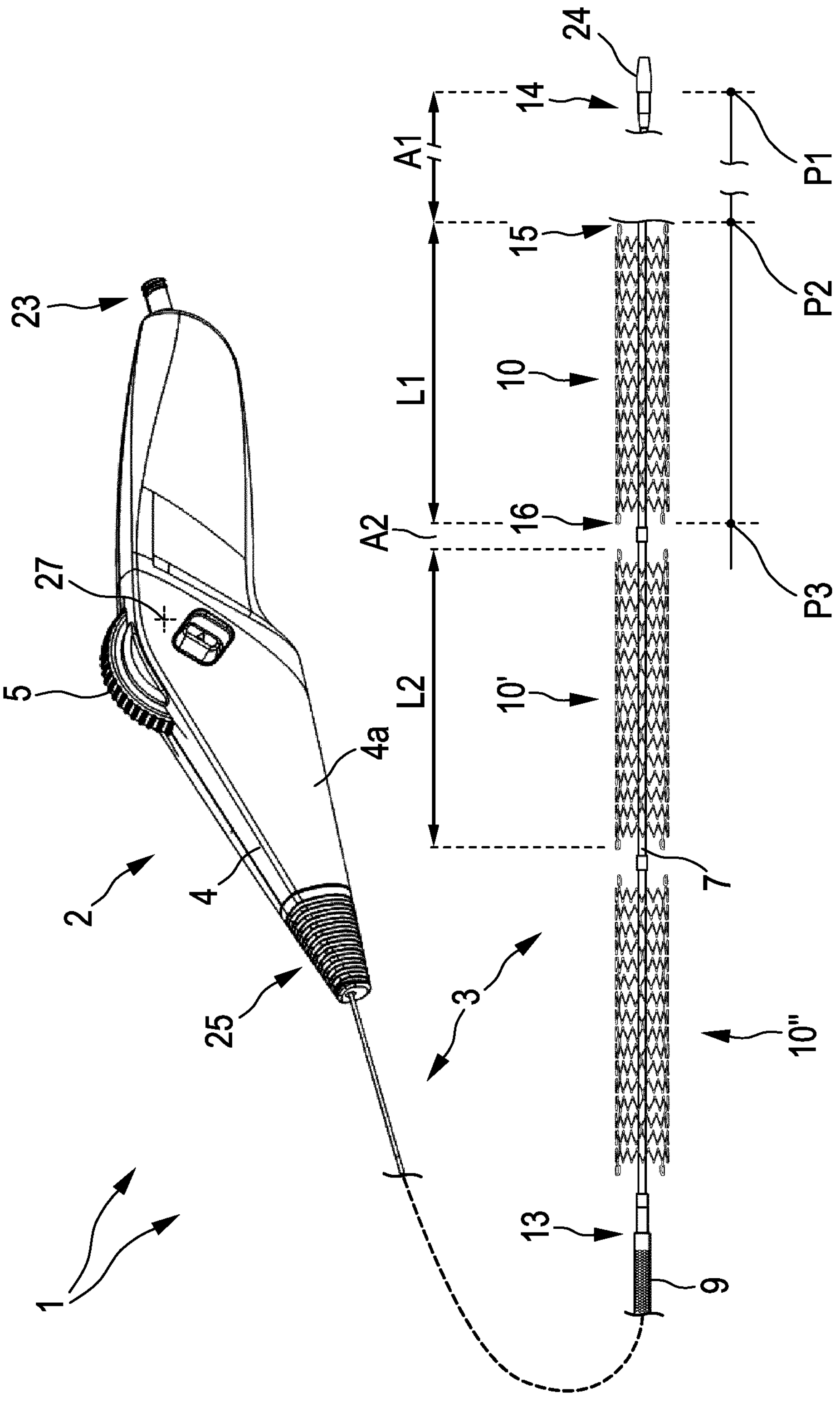
FIG. 1 is an isometric view an embodiment of a stent delivery system according to the invention, including an embodiment of a handling device according to the invention and a catheter arrangement with a plurality of stents, wherein the catheter arrangement is illustrated with partial sections.

According to FIG. 1, a stent delivery system 1 comprises a handling device 2 and a catheter arrangement 3. The stent delivery system 1 is intended for use in treatment of stenosis in blood vessels.

Figure 3:
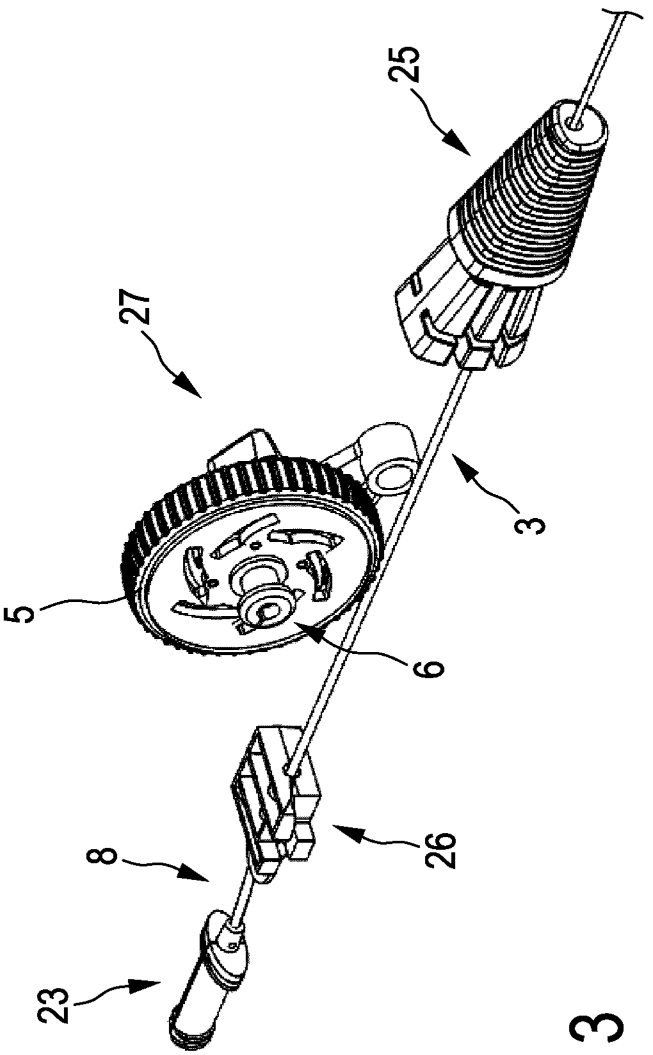
FIG. 3 shows the stent delivery system according to FIGS. 1 and 2 in a view corresponding to FIG. 2 with individual components and/or sections of the handling device hidden in the drawing.

The handling device 2 has a housing 4 with a thumbwheel 5 mounted in the housing 4 to be rotatable and a winding spool 6 rotating together with the thumbwheel 5 (FIG. 3, 4). The catheter arrangement 3 has an inner shaft 7 and an outer sheath 9 disposed coaxially to the inner shaft 7. A proximal end 8 of the inner shaft 7 is at least indirectly fixed on the housing 4 in a generally well-known manner. Further, the catheter arrangement 3 has at least a first stent 10 which is received radially between the inner shaft 7 and the outer sheath 9 in a condition of the catheter arrangement not illustrated in more detail in the drawing. Moreover, the stent delivery system 1 includes a flexible pull member 11 (FIG. 7) which, with one end, engages on a proximal end 12 of the outer sheath 9 and, with the other end, is held on the winding spool 6 to be windable. For release of at least the first stent 10, the outer sheath 9 is displaceable relative to the inner shaft 7 in the proximal direction by means of winding the flexible pull member 11 on the winding spool 6. The above mentioned release takes place starting from a displacement position of the outer sheath 9 not illustrated in more detail in the drawing, wherein a distal end 13 of the outer sheath 9 is essentially flush with a distal end 14 of the inner shaft. In this condition, the first stent 10 is compressed in the radial direction between an outer shell surface of the inner shaft 7 and an inner shell surface of the outer sheath 9. Following the above mentioned retraction of the outer sheath 9 in the proximal direction, the first stent 10 is released in the radial direction, and thereby may expand in the radial direction manner. With reference to FIG. 1, a corresponding released and expanded condition of the first stent 10 is illustrated.

Figure 5:
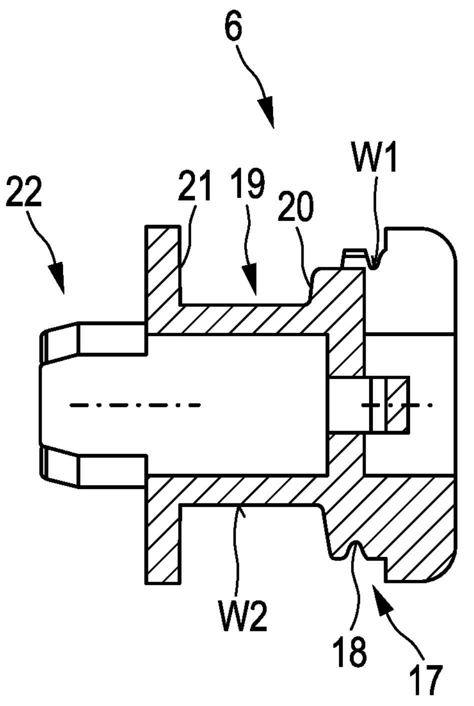
FIGS. 5 and 6 show the winding spool in a radial direction of viewing (FIG. 6) and in a longitudinal section V-V (FIG. 5) according to FIG. 6.
Figure 6:
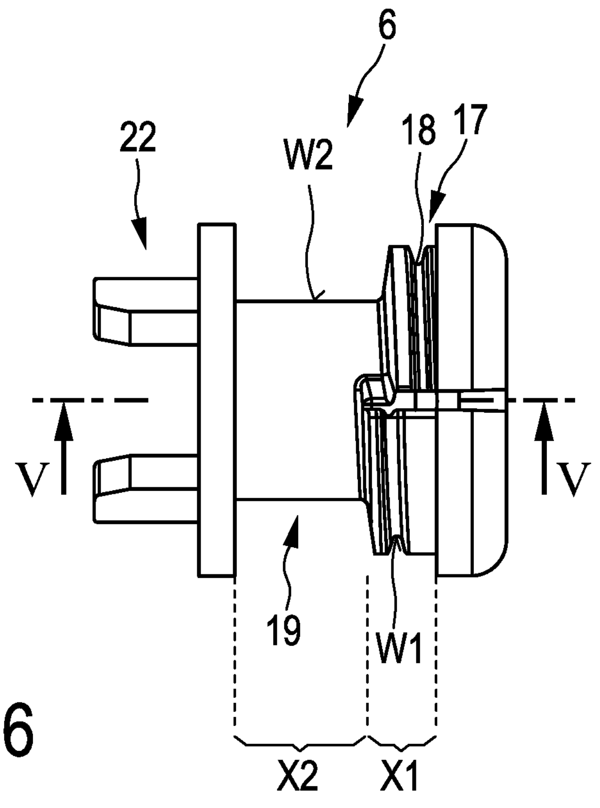

As shown in particular with reference to FIGS. 5 and 6, the winding spool 6 has different winding diameters W1, W2 on which the flexible pull member 11 engages and is windable in different displacement positions of the outer sheath 9, whereby different transmission ratios result between the rotation movement of the thumbwheel 5 and the proximal displacing movement of the outer sheath 9.

In the embodiment shown, the winding spool 6 has two different winding diameters W1, W2, namely a first winding diameter W1 and a second winding diameter W2.

For release of the first stent 10, the outer sheath 9 is moved relative to the inner shaft 7 starting from a first displacement position P1 in the proximal direction to a second displacement position P2 and, subsequently, further in the proximal direction to at least one third displacement position P3. The displacement positions P1, P2, P3 are schematically demonstrated with reference to FIG. 1. In the embodiment shown, the flexible pull member 11 cooperates with the first winding diameter W1 during a displacement of the outer sheath 9 between the first displacement position P1 and the second displacement position P2. That is, the flexible pull member 11 initially engages on the first winding diameter W1 and is wound thereon. During a further displacement of the outer sheath 9 from the second displacement position P2 to the third displacement position P3, the flexible pull member 11 cooperates with the second winding diameter W2. That is, the flexible pull member 11 engages on the second winding diameter W2 and is wound thereon. As a result, said different transmission ratios are obtained, namely a first transmission ratio during the displacement between the first displacement position P1 and the second displacement position P2, and a second transmission ratio during the further displacement between the second displacement position P2 and the third displacement position P3.

In the embodiment shown, the outer sheath 9, the inner shaft 7 and the first stent 10 are positioned in relation to each other in the different displacement positions of the outer sheath 9 as follows: In the first displacement position P1, the distal end 13 of the outer sheath 9 is oriented flush to the distal end 14 of the inner shaft 7. In the second displacement position P2, the distal end 13 of the outer sheath 9 is retracted relative to the distal end 14 of the inner shaft 7 in the proximal direction and is essentially flush with a distal end 15 of the first stent 10. In the third displacement position P3, the distal end 13, starting from the second displacement position P2, is retracted further in the proximal direction and is essentially flush with a proximal end 16 of the first stent 10. Correspondingly, the first stent 10 is received radially between the inner shaft 7 and the outer sheath 9, both in the first displacement position P1 and in the second displacement position P2. In contrast, in the third displacement position P3, the first stent 10 is released.

In the embodiment shown, the different winding diameters W1, W2 of the winding spool 6 are matched to different geometric properties of the catheter arrangement 3.

These geometric properties of the catheter arrangement 3 are, in the embodiment shown, a first axial distance A1 and a first length L1. The first axial distance A1 extends in the axial direction between the distal end 14 of the inner shaft 7 and the first stent 10, more precisely the distal end 15 thereof. In the present case, the first length L1 is the length of the first stent 10. Herein, the first winding diameter W1 is matched to the first axial distance A1 and the second winding diameter W2 is matched to the first length L1. In the present case, this matching is such that for displacing the outer sheath 9 along the first axial distance A1 and for bridging the first length L1, in each case exactly one revolution of the thumbwheel 5 and, thus, also of the winding spool 6 are required. For that purpose the first winding diameter W1 has a perimeter which corresponds to the axial distance Aland the second winding diameter W2 has a perimeter which corresponds to the first length L1 of the first stent 10.

In the embodiment shown, the catheter arrangement 3 has further stents 10', 10", in addition to the first stent 10, namely a second stent 10' and a third stent 10". Of course, such a configuration is not mandatory. The second stent 10' and the third stent 10" are received in the radial direction between the inner shaft 7 and the outer sheath 9, in a manner corresponding to the first stent 10, again not illustrated herein, and releasable by means of a displacement of the outer sheath 9 passing beyond the third displacement position P3 in the proximal direction.

In a not shown embodiment, as an alternative or in addition, the different winding diameters of the winding spool are matched to a second axial distance A2 between the first stent 10 and the second stent 10' and/or a second length L2 of the second stent 10'.

Before discussing the further specific configuration of the handling device 2 and the catheter arrangement 3, the further features of the winding spool 6 are explained, in particular with reference to FIGS. 5 and 6:

The figures show that the different winding diameters W1, W2 are provided on different axial sections X1, X2 of the winding spool 6. The first winding diameter W1 is formed on a first axial section X1 and the second winding diameter W2 is formed on a second axial section X2 of the winding spool 6. The axial sections X1, X2 are disposed adjacent to each other in the axial direction of the winding spool 6. In the present case, during the proximal displacement of the outer sheath 9 starting from the first displacement position P1, the flexible pull member 11 cooperates initially with the first axial section X1. Subsequently, namely after reaching the second displacement position P2 of the outer sheath 9, the flexible pull member 11 cooperates with the second axial section X2. Put in other words, the flexible pull member 11 is initially wound on the first winding diameter W1 of the first axial section X1 and then enters, namely after reaching the second displacement position P2 of the outer sheath 9, the second axial section X2 and there is wound on the second winding diameter W2.

Further, the winding spool 6 has a helical circumferential groove 17, with the groove bottom 18 thereof providing the first winding diameter W1. The circumferential groove 17 extends along the circumference of the first axial section X1 and has a pitch oriented in the axial direction of the winding spool 6, as a result of which said helical shape of the circumferential groove 17 is obtained. This configuration allows in particular precise guiding of the flexible pull member 11 during winding on the first winding diameter W1.

Further, the winding spool 6 has a cylindrical section 19, with the outer diameter thereof providing the second winding diameter W2. The cylindrical section 19 has a straight circular cylinder shape, in the present case.

In the embodiment shown, the first winding diameter W1 is larger than the second winding diameter W2. Apart from that, an outer diameter of the thumbwheel 5, not described in more detail, is greater than the first winding diameter W1.

In the present case, a first radial shoulder 20 is disposed in the axial direction between the first axial section X1 and the second axial section X2. The first radial shoulder 20 forms a step between the first winding diameter W1 and the second winding diameter W2 such that, during winding of the flexible pull member 11, a quasi-abrupt transition results, and not a continuous variation of the transmission ratio.

Moreover, in the present case, the winding spool 6 has a second radial shoulder 21 which forms an axial boundary of the second axial section X2 and, thus, also of the cylindrical section 19. In this respect, the second axial section X2 extends in the axial direction between the two shoulders 20, 21.

In the present case, the winding spool 6 moreover has a fastening section 22 which is provided for torque-transmitting fastening of the winding spool 6 on the thumbwheel 5, and cooperates with a complementary fastening section of the thumbwheel 5, not illustrated in more detail. The fastening section 22 is disposed on a front end region of the winding spool 6 facing away from the first winding diameter W1.

Further details of the configuration of the handling device 2 and the catheter arrangement 3 will be discussed below, however, are not to be considered as mandatory features in view of the present invention.

Figure 2:
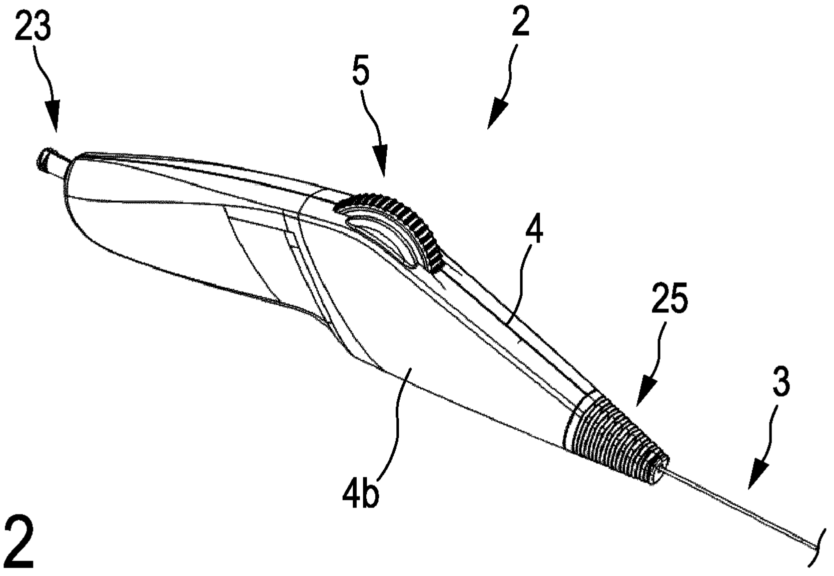
FIG. 2 shows the stent delivery system according to FIG. 1 in the region of the handling device in a further isometric view.

In the present case, the housing 4 has two housing halves 4*a*, 4*b*, namely a first housing half 4*a* (FIG. 1) and a second housing half 4*b*. In the ready-for-use condition of the stent delivery system 1, shown with reference to the FIGS. 1 and 2, the housing halves 4*a*, 4*b* are joined together in a generally well-known manner. In the present case, the housing 4 is manufactured from a dimensionally stable synthetic material. As is further apparent with reference to the FIGS. 1 and 2, the housing 4 provides a handle which may be grasped by a hand such that the thumb of the respective hand is placed in the region of an upper side of the housing 4 for rotating actuation of the thumbwheel 5.

Figure 4:
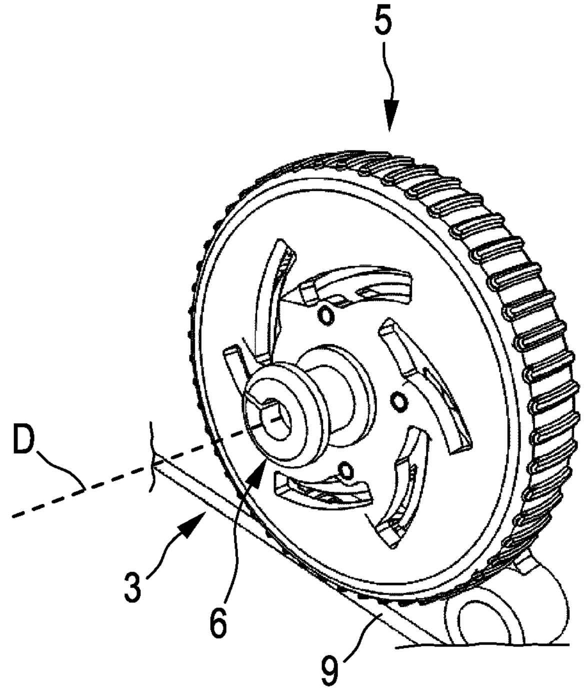
FIG. 4 is an enlarged detail illustration of the view according to FIG. 3 in the region of a thumbwheel and a winding spool operatively connected to the thumbwheel.

The thumbwheel 5 is mounted in the housing 4 to be rotatable about a rotation axis D (FIG. 4) and protrudes, in the radial direction of the thumbwheel 5, from a recess of the housing 4 not described in more detail. As a result, the thumbwheel 5 is manually operable in the above described manner. The rotation axis D is perpendicular to the proximal displacement direction of the outer sheath 9 and—during conventional handling—in approximately horizontal orientation, in the embodiment shown.

The winding spool 6 is oriented coaxially to the thumbwheel 5 and connected to the thumbwheel 5 by the fastening section 22 (FIG. 5) in a torque-transmitting manner. As a result, the winding spool 6 is rotatable together with the thumbwheel 5 about the rotation axis D. In a not shown embodiment, the winding spool 6 can be provided integrally with the thumbwheel 5. In the embodiment shown, the winding spool 6 is disposed completely inside the housing 4.

The catheter arrangement 3 extends in the region of the handling device 2 between a distal end and a proximal end of the housing 4 within the latter. The inner shaft 7 includes a lumen, not apparent in more detail, which extends between the proximal end 8 and the distal end 14. In the region of the proximal end 8, the lumen leads into a Luer port 23 which is fixed to the proximal end of the housing 4 in a generally well-known manner. On its distal end 14, the inner shaft 7 includes a catheter tip 24. The inner shaft 7 has a flexible design. The outer sheath 9 is manufactured from a braided material and connected in the region of its proximal end 12 (FIG. 7) to the flexible pull member 11 for transfer of pulling force. In the embodiment shown, the first stent 10 is a self-expanding stent manufactured and designed in a manner known to the skilled person. The same applies to the second stent 10' and the third stent 10".

Further, in the present case, the handling device 2 includes a guiding tip 25 which is disposed on a distal end of the housing 4 and is held between the housing halves 4*a*, 4*b*. The catheter arrangement 3 extends, in the region of the distal end of the housing 4, through the guiding tip 25 in the axial direction.

Figure 7:
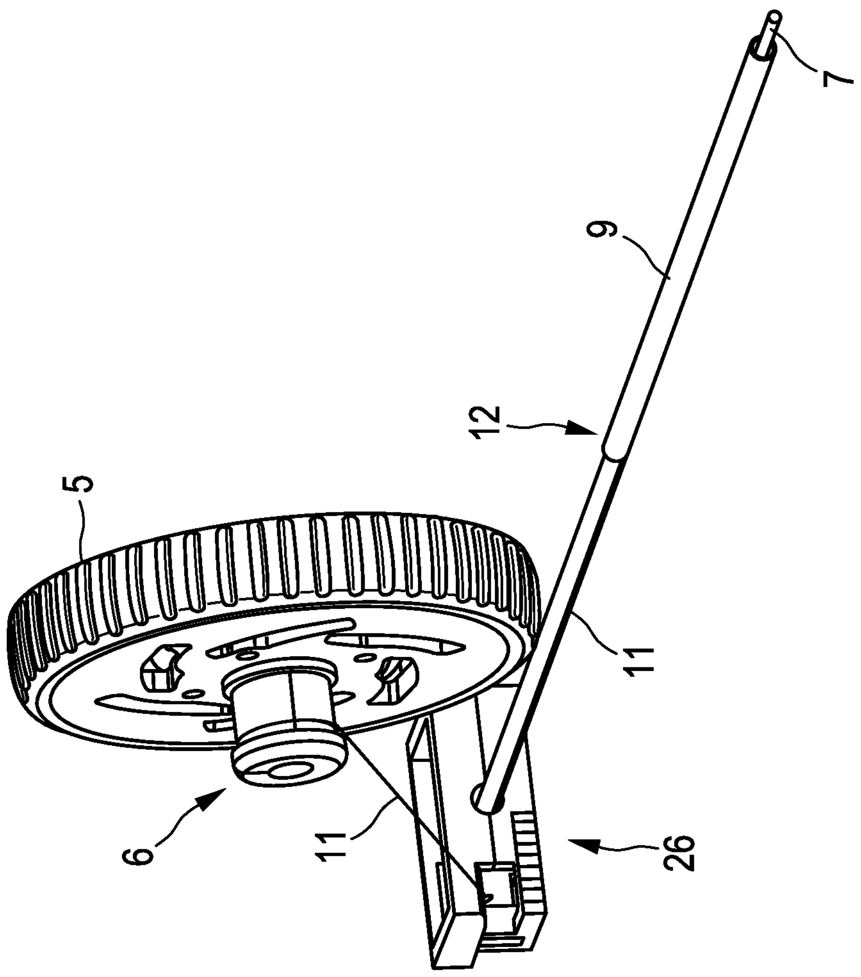
FIG. 7 is another isometric view similar to FIG. 3 and additionally showing a flexible pull member which engages, with one end, on the catheter arrangement and, with the other end, is held on the winding spool to be windable.

Furthermore, the handling device 2 includes a deflecting and tensioning device 26 which is disposed in the axial direction of the catheter arrangement 3 between the thumbwheel 5—and, thus, also the winding spool 6—and the proximal end 8 of the inner shaft 7. The deflecting and tensioning device 26 is intended for deflecting and tensioning of the flexible pull member 11 (FIG. 7). Moreover, a locking and unlocking mechanism 27 is provided which is intended for locking and unlocking the rotational mobility of the thumbwheel 5 and, thus, also the winding spool 6. Neither the deflecting and tensioning device 26 nor the locking and unlocking mechanism 27 are mandatory, therefore, a more detailed description thereof is omitted for reasons of brevity.

The invention claimed is:

1. A stent delivery system comprising:

a handling device having a housing, a thumbwheel rotatably mounted in the housing, and a winding spool rotatable together with the thumbwheel;

a catheter arrangement having an inner shaft, with a proximal end of the inner shaft fixed on the housing, an outer sheath disposed coaxially to the inner shaft, and having at least a first stent which is received radially between the inner shaft and the outer sheath; and a flexible pull member having a first end and a second end, the first end engaging on a proximal end of the outer sheath, and the second end held on the winding spool to be windable;

wherein, for release of at least the first stent, the outer sheath is displaceable relative to the inner shaft in a proximal direction by winding the flexible pull member on the winding spool, and wherein the winding spool has different winding diameters on which the flexible pull member engages and is windable in different displacement positions of the outer sheath, whereby different transmission ratios result between a rotational movement of the thumbwheel and a proximal displacing movement of the outer sheath, wherein the different winding diameters comprise at least a first winding diameter on which the flexible pull member engages during a displacement of the outer sheath between a first displacement position and a second displacement position, and a second winding diameter on which the flexible pull member engages during a displacement of the outer sheath between the second displacement position and a third displacement position, wherein the winding spool has a helical circumferential groove and a groove bottom, the groove bottom providing the first winding diameter, and wherein the winding spool has a cylindrical section comprising an outer diameter, with the outer diameter providing the second winding diameter.

2. The stent delivery system according to claim 1, wherein each of the different winding diameters of the winding spool has a perimeter equal to a length of a respective different length property of the catheter arrangement.

3. The stent delivery system according to claim 2, wherein each different length property comprises one of:

a first axial distance between a distal end of the inner shaft and the first stent, a first length of the first stent, a second axial distance between the first stent and a second stent, or a second length of the second stent.

4. The stent delivery system according to claim 1, wherein the different winding diameters are formed on different axial sections of the winding spool.

5. The stent delivery system according to claim 1, wherein the helical circumferential groove is configured such that exactly one revolution of the thumbwheel is required to retract the outer sheath from the first displacement position to the second displacement position in order to retract the outer sheath to a distal end of the first stent.

6. The stent delivery system according to claim 1, wherein the cylindrical section is configured such that exactly one revolution of the thumbwheel is required to retract the outer sheath from the second displacement position to the third displacement position in order to release the first stent.

7. A handling device for a stent delivery system, the handling device comprising:

a housing;

a thumbwheel rotatably mounted in the housing; and a winding spool rotatable together with the thumbwheel, the winding spool comprising different winding diameters, wherein the different winding diameters comprise at least a first winding diameter, and a second winding diameter, wherein the winding spool has a helical circumferential groove and a groove bottom, the groove bottom providing the first winding diameter, and wherein the winding spool has a cylindrical section comprising an outer diameter, with the outer diameter providing the second winding diameter.

* * * * *